United States Patent
Chen et al.

(10) Patent No.: US 11,648,066 B2
(45) Date of Patent: May 16, 2023

(54) METHOD AND SYSTEM OF DETERMINING ONE OR MORE POINTS ON OPERATION PATHWAY

(71) Applicant: Brain Navi Biotechnology Co.,Ltd., Hsinchu (TW)

(72) Inventors: Chieh Hsiao Chen, Santa Clara, CA (US); Kuan Ju Wang, Santa Clara, CA (US)

(73) Assignee: BRAIN NAVI BIOTECHNOLOGY CO. LTD., Zhubei (TW)

( * ) Notice: Subject to any disclaimer, the term of this patent is extended or adjusted under 35 U.S.C. 154(b) by 836 days.

(21) Appl. No.: 16/490,876

(22) PCT Filed: Jun. 4, 2018

(86) PCT No.: PCT/CN2018/089769
§ 371 (c)(1),
(2) Date: Sep. 3, 2019

(87) PCT Pub. No.: WO2018/223925
PCT Pub. Date: Dec. 13, 2018

(65) Prior Publication Data
US 2020/0008892 A1    Jan. 9, 2020

Related U.S. Application Data

(60) Provisional application No. 62/618,053, filed on Jan. 16, 2018, provisional application No. 62/612,728, (Continued)

(51) Int. Cl.
*A61B 34/20*   (2016.01)
*A61B 34/30*   (2016.01)
(Continued)

(52) U.S. Cl.
CPC .............. *A61B 34/30* (2016.02); *A61B 34/20* (2016.02); *A61B 90/361* (2016.02);
(Continued)

(58) Field of Classification Search
CPC ....... A61B 34/30; A61B 34/20; A61B 90/361; A61B 2034/2068; A61B 2090/371;
(Continued)

(56) References Cited

U.S. PATENT DOCUMENTS

2014/0112529 A1    4/2014   Park et al.
2014/0232824 A1    8/2014   DiMaio et al.
(Continued)

FOREIGN PATENT DOCUMENTS

CN            103961178 B         5/2016

OTHER PUBLICATIONS

The International Search Report and Written Opinion of the International Search Authority for the International Application No. PCT/CN2018/089769 dated Sep. 7, 2018.

*Primary Examiner* — Joel Lamprecht
(74) *Attorney, Agent, or Firm* — Haverstock & Owens

(57) ABSTRACT

Embodiments of the present invention set forth a method to drive robotic arm to one or more points on an operation pathway. The method includes constructing a three-dimensional model based on a medical image scan of a patient, planning an operation pathway according to the three-dimensional model, retrieving image information of the patient captured by a three-dimensional optical apparatus, selecting a first set of landmark points in the three-dimensional model, selecting a second set of landmark points in the retrieved image information, matching the first set of landmark points with the second set of landmark points, transforming coordinates from a three-dimensional model coordinate system to a three-dimensional optical apparatus
(Continued)

coordinate system based on a result of the matching, and driving the robotic arm to the one or more points on the operation pathway in a robotic arm coordinate system.

23 Claims, 14 Drawing Sheets

Related U.S. Application Data filed on Jan. 2, 2018, provisional application No. 62/514,951, filed on Jun. 4, 2017.

(51) Int. Cl.
*A61B 90/00* (2016.01)
*G06T 7/00* (2017.01)
*G06T 17/20* (2006.01)

(52) U.S. Cl.
CPC .......... *G06T 7/0012* (2013.01); *G06T 17/205* (2013.01); *A61B 2034/2068* (2016.02); *A61B 2090/371* (2016.02); *A61B 2090/3762* (2016.02)

(58) Field of Classification Search
CPC ............ A61B 2090/3762; A61B 34/10; A61B 2034/105; A61B 2034/107; A61B 2090/364; A61B 2090/374; A61B 2090/363; G06T 7/0012; G06T 17/205
See application file for complete search history.

(56) References Cited

U.S. PATENT DOCUMENTS

| | | | |
|---|---|---|---|
| 2015/0173715 A1* | 6/2015 | Raghavan | G16H 40/67 600/443 |
| 2016/0022146 A1* | 1/2016 | Piron | A61B 5/055 600/411 |
| 2016/0027342 A1* | 1/2016 | Ben-Haim | G09B 5/02 434/272 |
| 2016/0067525 A1 | 3/2016 | Bouchet et al. | |
| 2016/0070436 A1* | 3/2016 | Thomas | A61B 8/0808 715/771 |
| 2016/0100908 A1* | 4/2016 | Tesar | A61B 1/24 600/202 |

\* cited by examiner

METHOD AND SYSTEM OF DETERMINING ONE OR MORE POINTS ON OPERATION PATHWAY

CROSS-REFERENCE TO RELATED APPLICATIONS

This application claims the benefit of U.S. Provisional Application No. 62/514,951, filed Jun. 4, 2017, U.S. Provisional Application No. 62/612,728, filed Jan. 2, 2018, and U.S. Provisional Application No. 62/618,053, filed Jan. 16, 2018, which are incorporated by reference in their entirety.

BACKGROUND OF THE INVENTION

Field of the Invention

Embodiments of the present invention relate generally to methods and systems of determining one or more points on an operation pathway.

Description of the Related Art

Unless otherwise indicated herein, the approaches described in this section are not prior art to the claims in this application and are not admitted to be prior art by inclusion in this section.

In an operation, a plan of an operation pathway is critical. The operation pathway may include multiple points, such as a safety point and a preoperative point away from the patient, an entry point on patient's tissues, and a target point at the target of the operation.

Robotic operation may offer a precise control of the operation pathway. Before the operation, patient is subjected to a medical scan (e.g., CT or MRI). The operation pathway to the desired anatomical region is planned. Artificial intelligence may be employed to suggest the surgeon with best routes that incur the least amount of damages. To perform the operation, the position of the patient may be matched to the perspective of the medical scan to accurate perform the operation along the planned operation pathway. Conventional approaches have relied on glued on or screwed in fiducial marks, which has adoption issues.

DETAILED DESCRIPTION

Figure 1:
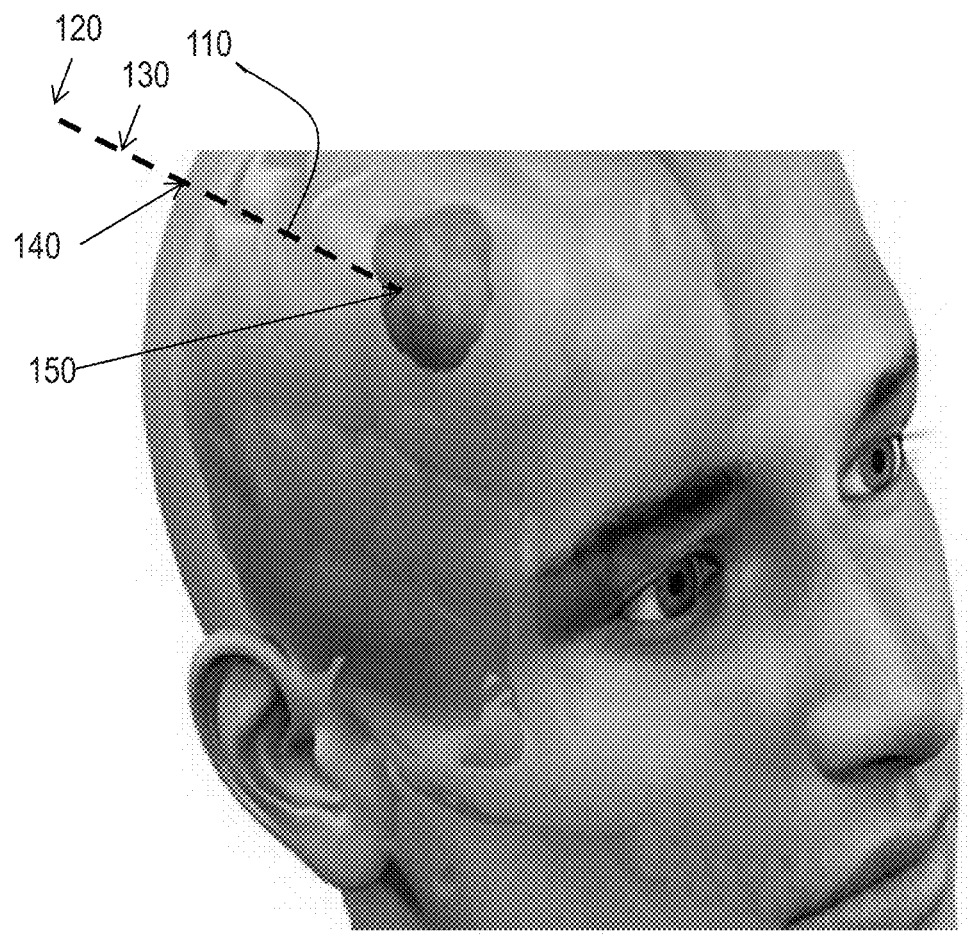
FIG. 1 is an example figure showing the spatial relationships among several points that may be encountered during an operation.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

FIG. 1 is an example figure showing the spatial relationships among several points that may be encountered during an operation, arranged in accordance with some embodiments of the present disclosure. In FIG. 1, an operation pathway 110 may include safety point 120, preoperative point 130, entry point 140, and target point 150.

Figure 2:
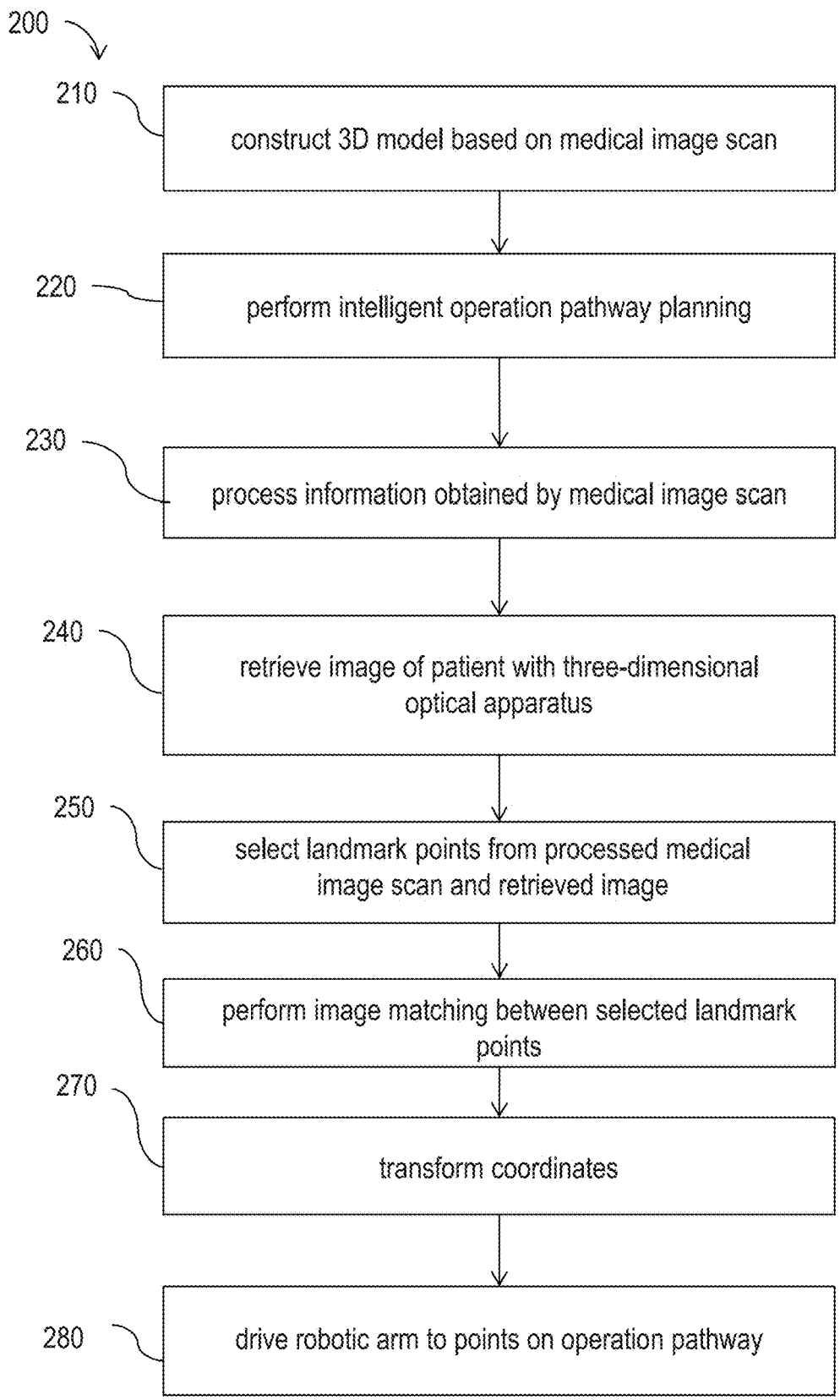
FIG. 2 is a flow diagram illustrating an example process to drive robotic arm to one or more points on an operation pathway.

FIG. 2 is a flow diagram illustrating an example process 200 to drive robotic arm to one or more points on an operation pathway, arranged in accordance with some embodiments of the present disclosure. Process 200 may include one or more operations, functions, or actions as illustrated by blocks 210, 220, 230, 240, 250, 260, 270, and/or 280, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 200 may begin at block 210, "construct three-dimensional model based on medical image scan." Before an operation is performed, some medical imaging techniques may be used to capture a snapshot of a patient's conditions, so that an operation plan may be formulated. The operation plan may include a planned operation pathway as set forth above. For example, the surgeon may order a medical image scan (e.g., CT or MRI) of the operation target. Such a medical image scan may be performed a few days (e.g., 3 to 5 days) prior to the operation. A three-dimensional model may be constructed based on the medical image scan data using some known approaches. Accordingly, points on the planned operation pathway may be identified in the three-dimensional model.

Figure 3:
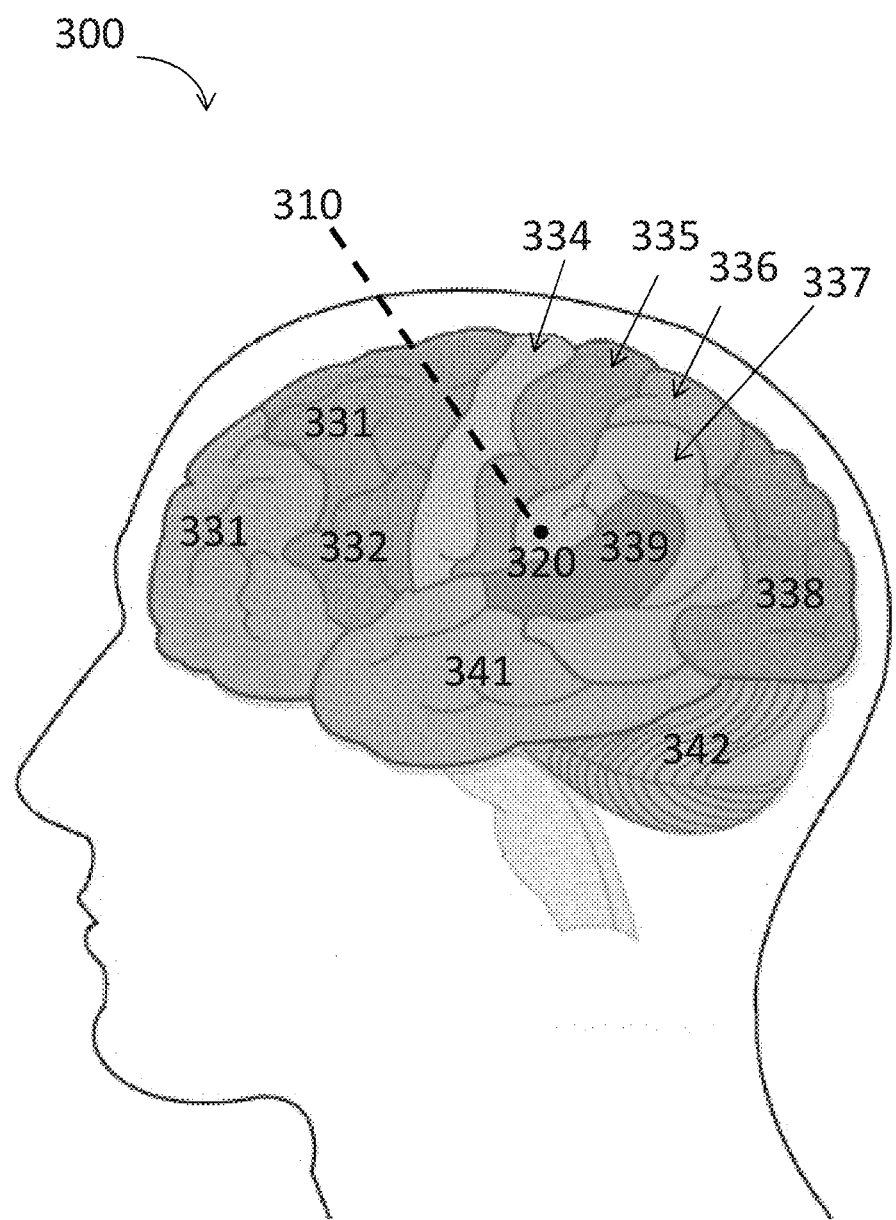
FIG. 3 illustrates an example of the operation pathway calculation.

Block 210 may be followed by block 220 "perform intelligent operation pathway planning." In some embodiments, an artificial intelligence engine may be employed to suggest the surgeon with one or more routes with minimized physical damages to the patient. Based on the patient's CT or MRI scan, the artificial intelligence engine may suggest one or more optimal operation pathway. FIG. 3 illustrates an example of a calculation of operation pathway 310 to reach target point 320, arranged in accordance with some embodiments of the present disclosure. The calculation may include transforming the standard brain-atlas data, and registering it to the patient's medical scan images to identify the brain regions. Some example brain regions include motor association area 331, expressive speech area 332, higher mental functions area 333, motor area 334, sensory area 335, somatosensory association area 336, global language area 337, vision area 338, receptive speech area 338, receptive speech area 339, association area 341, and cerebellum area 342. Moreover, common target tissues, such as sub-thalamic nucleus, may be automatically identified. In addition, each brain region set forth above may be assigned with a cost function for the artificial intelligence engine to suggest one or more routes to the target tissues. The blood vessels may be identified from the TOF (time-of-flight MRI) data. The points on the outer brain boundary are candidate for entry point.

Figure 4A:
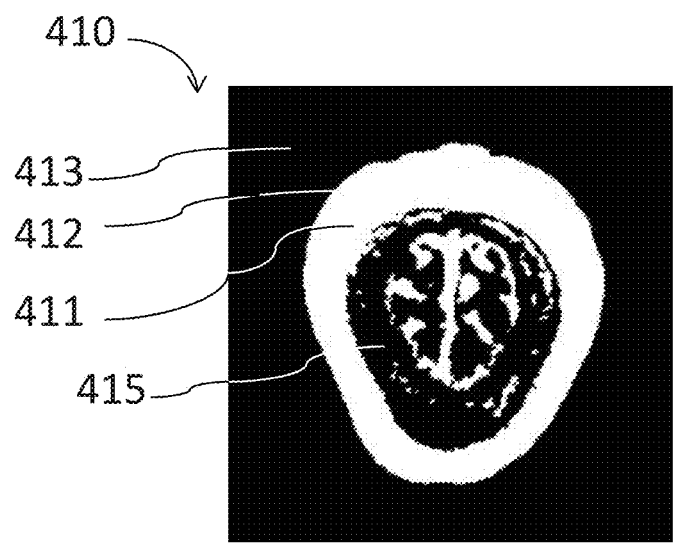
FIGS. 4A and 4B illustrate an image processing to process information obtained by a medical image scan.
Figure 4A:
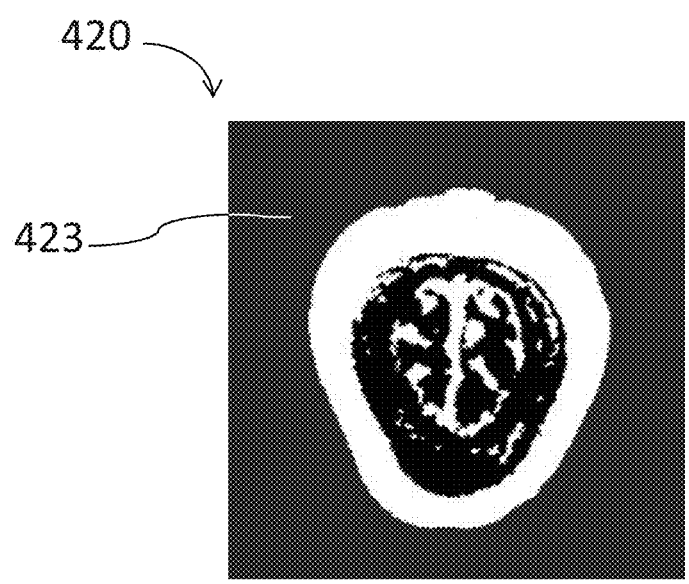
Figure 4B:
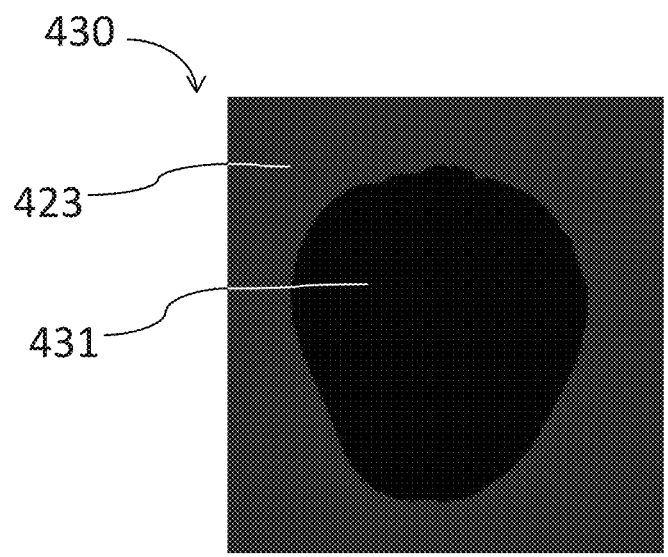
Figure 4B:
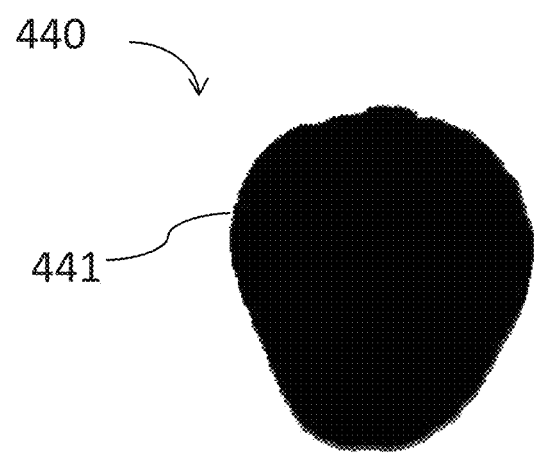

FIGS. 4A and 4B illustrate an image processing to process information obtained by the medical image scan, arranged in accordance with some embodiments of the present disclosure. In conjunction with FIGS. 4A and 4B, block 220 may be followed by block 230, "process information obtained by medical image scan," in accordance with some embodiments of the present disclosure. The points obtained from the images captured by a three-dimensional optical apparatus are only associated with the patient's appearance information but are not associated with the patient's under-skin information. However, images obtained by medical image scan usually are associated with both the appearance and the under-skin information. Image processing is performed to remove the under-skin information from the medical image scan. Therefore, in block 260, the appearance points obtained by the three-dimensional optical apparatus and the appearance points obtained from the medical image scan are used for the three-dimensional matching.

In FIG. 4A, in some embodiments, assuming the operation target is inside the patient's head, binary image 410 may be derived from an original MRI image along an axial direction from head to toes of the patient. Region 411 is the skull of the patient and is usually represented in white in the original MRI image. The outer periphery 412 of region 411 may refer to the patient's skin, which is associated with the patient's appearance. With thresholding approach, image 410 including region 413 outside of the skull (all black) and region 415 inside the skull may be created. Image 410 may be further processed to form image 420. In image 420, region 413 is assigned a gray scale to be differentiated from black and white to form region 423.

In FIG. 4B, image 420 may be further processed to form image 430. In image 430, regions other than the gray scale of region 413 are assigned with black to form region 431. Region 423 in image 430 may then be assigned with white to form image 440. In some embodiments, points along periphery 441 of image 440 may be selected for matching points from images taken by the three-dimensional optical apparatus in block 240.

Block 230 may be followed by block 240 "retrieve image of patient taken by three-dimensional optical apparatus." The "three-dimensional optical apparatus" may generally refer to a camera or a scanner with depth sensing technologies. In some embodiments, the three-dimensional optical apparatus may include, but not limited to, at least two two-dimensional cameras. In some other embodiments, the three-dimensional optical apparatus may include, but not limited to, a three-dimensional depth sensing module and a two-dimensional camera module. In some embodiments, the three-dimensional scanner is configured to create a point cloud of geometric samples on a surface of an object to be scanned. These points may be used to extrapolate the shape of the object. In some embodiments, the three-dimensional scanner may be an intraoral scanner.

In some embodiments, in addition to information obtained with traditional two-dimensional optical apparatus, the three-dimensional optical apparatus may capture the depth information of the patient. In some embodiments, the three-dimensional optical apparatus may be configured to take images of the patient immediately prior to a surgical incision is made on the patient in the operating room. The three-dimensional optical apparatus may be fixed at a stationary device (e.g., a robotic arm, an operating trolley) in the operating room.

Block 240 may be followed by block 250 "select landmark points." In some embodiments, one or more landmark points may be selected from the three-dimensional model constructed in block 210 and the image retrieved in block 240. In some embodiments, 3 or more landmark points with strong features are selected. Examples of landmark points may include middle of eyes, nose tip, or mouth. In some embodiments, 3 landmark points may identify an initial three-dimensional coordinate that allows subsequent matching using iterative closest point (ICP) algorithm. In some embodiments, the landmark points may be in the same order in both the three-dimensional optical apparatus scan and the CT/MRI data (for example, 1. nose tip, 2. left eye, 3. right eye).

For clarity, the following discussions mainly use one non-limiting example of the three-dimensional optical apparatus, e.g., a three-dimensional camera, and its coordinate system, e.g., three-dimensional camera coordinate system, to explain various embodiments of the present disclosure.

Figure 5A:
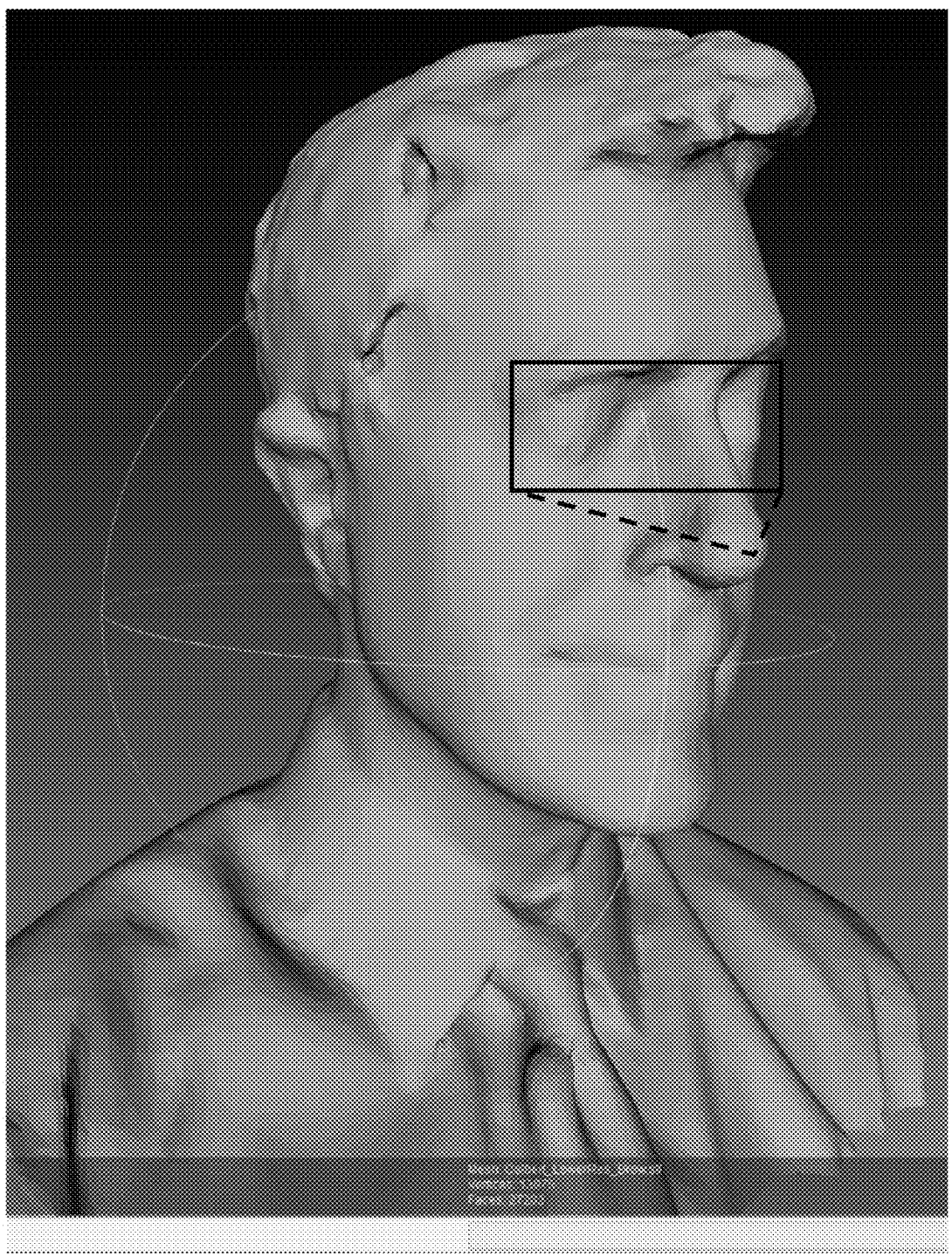
FIGS. 5A and 5B illustrate facial recognition method of selecting key features to identify landmark points.
Figure 5B:
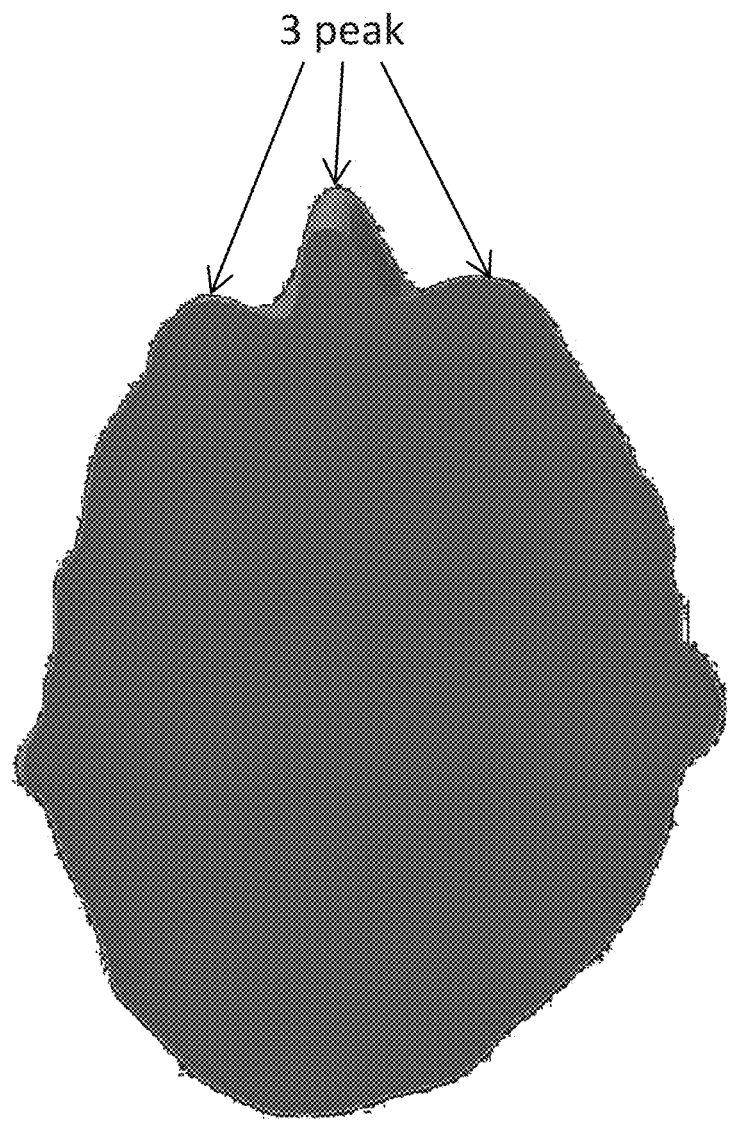

In some embodiments, FIGS. 5A and 5B illustrate facial recognition methods of selecting key features to identify landmark points, arranged in accordance with some embodiments of the disclosure. Because a patient typically closes his or her eyes during surgical procedures, traditional facial recognition algorithms that rely on identifying his or her eyes with round irises cannot be used. Instead, the patient's nose, the most anterior structure, may be selected first. This is possible because the patient generally lies in the same position. From the nose tip with pre-determined z-offset, a region of interest (e.g., the rectangle illustrated in FIG. 5A) is defined for selecting other landmark points (e.g., eyes). In some embodiments, the region of interest may include a region defined by the nose tip, the eyes, the forehead, and a region between the eyebrows. Accordingly, in some embodiments, from transverse (axial) cross sections, 3 or more landmark points may be identified (e.g., nose as the taller center peak, and the eye-balls as the smaller 2 peaks).

Block 250 may be followed by block 260, "perform image matching." In some embodiments, the image matching includes matching the landmark points selected in block 250. In some embodiments, the landmark points selected from the images taken by the three-dimensional optical apparatus and the landmark points selected from the constructed three-dimensional model are matched, sometimes iteratively to minimize the differences between the two sets of landmark points. In some embodiments, the landmark points used for matching may encompass all the available surface data. In other embodiments, the landmark points used for matching may be a chosen subset of the surface data. For example, the landmark points for matching may be repeatedly selected from the region of interest (e.g., the rectangle illustrated in FIG. 5A) of the images taken by the three-dimensional optical apparatus and the region of interest of the constructed three-dimensional model, instead of repeatedly selecting from all the available surface data.

Block 260 may be followed by block 270, "transform coordinates." In block 270, selected points from the constructed three-dimensional model (e.g., P1, P2 and P3) are transformed from their original coordinate system (i.e., three-dimensional model coordinate system) to the coordinates of the images taken by the three-dimensional optical apparatus (i.e., three-dimensional camera coordinate system). The transformation may be based on some image comparison approaches, such as iterative closest point (ICP). Block 270 may further include additional coordinate transformations in which all points on the three-dimensional camera coordinate system are transformed to the coordinates of the robotic arm (i.e., robotic arm coordinate system). The details of transforming coordinates will be further described below.

Block 270 may be followed by block 280, "drive robotic arm to points on operation pathway." In block 280, the coordinates of the planned operation pathway in three-dimensional model coordinate system may be transformed to the robotic arm coordinate system. Therefore, the robotic arm may move to the safety point, the preoperative point, the entry point, and/or the target point on the planned operation pathway.

In sum, a three-dimensional camera or scanner may be used to obtain a patient's facial features. The facial features may then be compared with processed image data associated with a medical image scan. To compare, landmark points are selected in the same sequence in both the images obtained by the three-dimensional camera and the images associated with the medical image scan. In some embodiments, example process 200 may be applied to various types of operations, such as brain operations, nervous system operations, endocrine operations, eye operations, ears operations, respiratory operations, circulatory system operations, lymphatic operations, gastrointestinal operations, mouth and dental operations, urinary operations, reproductive operations, bone, cartilage and joint operations, muscle/soft tissue operations, breast operations, skin operations, and etc.

Figure 6:
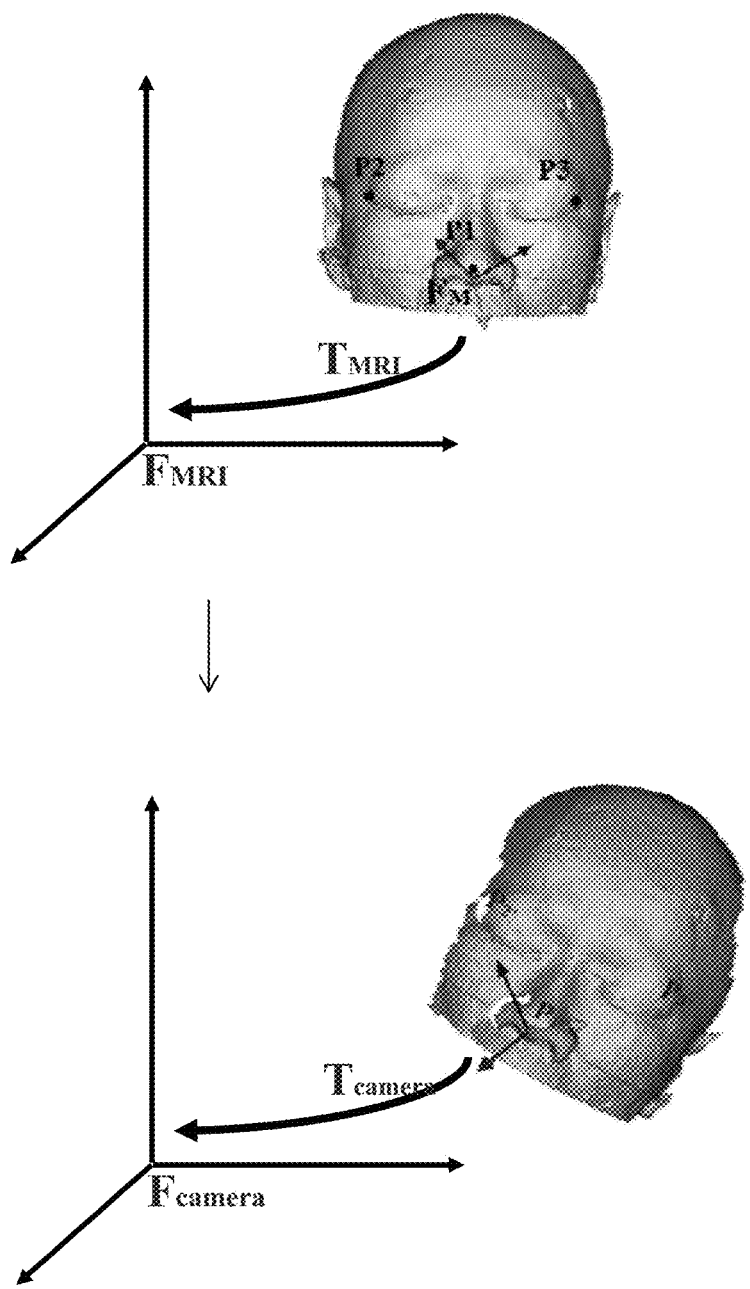
FIG. 6 illustrates coordinate transformation from the constructed three-dimensional model coordinate system to the three-dimensional camera coordinate system.

FIG. 6 illustrates an example coordinate transformation from the constructed three-dimensional model coordinate system to the three-dimensional camera coordinate system, in accordance with some embodiments of the present disclosure. This figure will be further discussed below in conjunction with FIG. 7.

Figure 7:
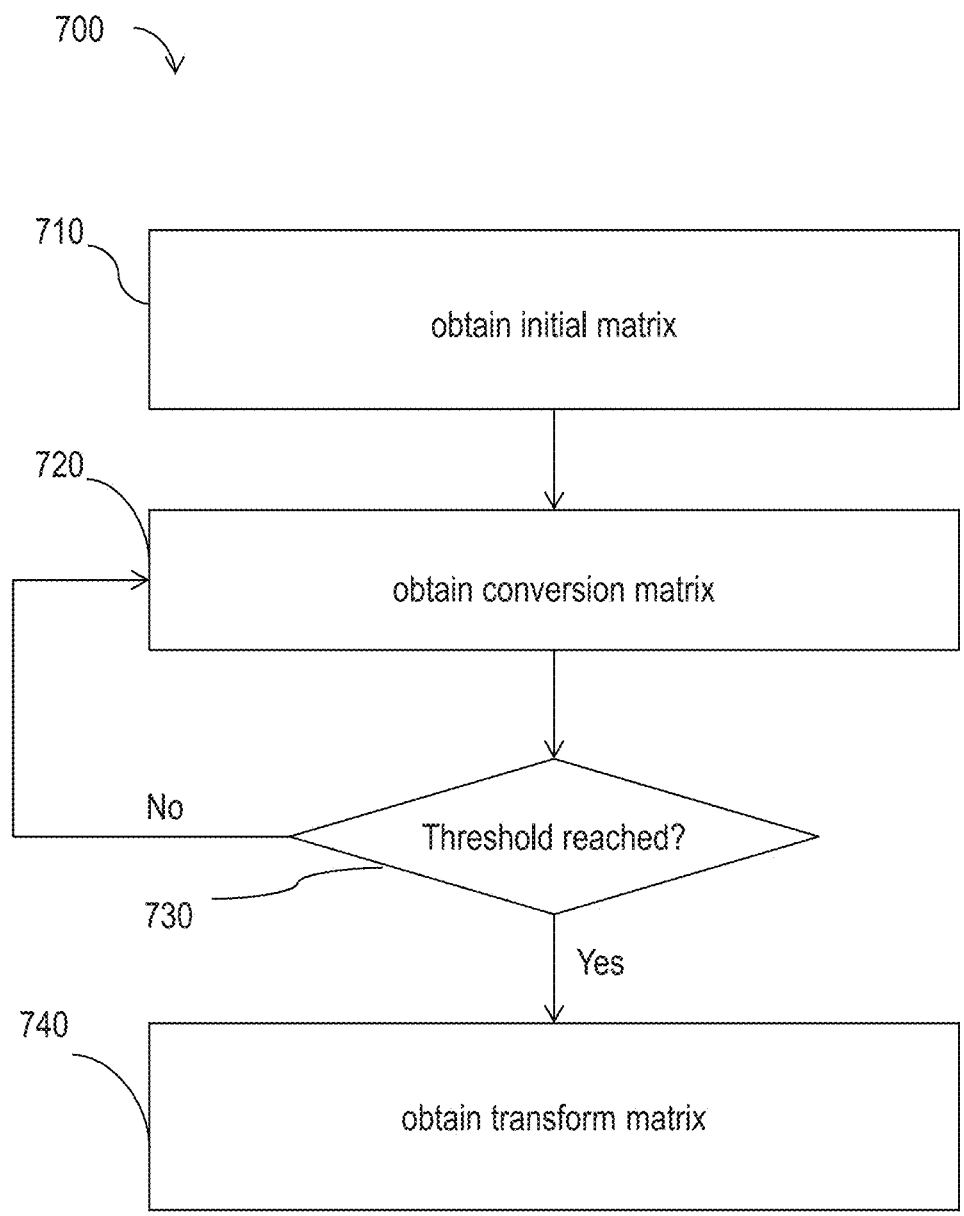
FIG. 7 is a flow diagram illustrating an example process to transform coordinates.

FIG. 7 is a flow diagram illustrating an example process 700 to transform coordinates, in accordance with some embodiments of the present disclosure. Process 700 may include one or more operations, functions, or actions as illustrated by blocks 710, 720, 730, and/or 740, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

In conjunction with FIG. 6, in block 710, initial matrices are obtained. In some embodiments, a first initial matrix $T_{MRI}$ and a second initial matrix $T_{camera}$ are obtained. In some embodiments, $$TMRI = \begin{bmatrix} Vector_{X_x} & Vector_{Y_x} & Vector_{Z_x} & P_{1x} \\ Vector_{X_y} & Vector_{Y_y} & Vector_{Z_y} & P_{1y} \\ Vector_{X_z} & Vector_{Y_z} & Vector_{Z_z} & P_{1z} \\ 0 & 0 & 0 & 1 \end{bmatrix} \quad (1)$$

in which $$P_1P'_{2_{norm}} \times P_1P'_{3_{norm}} = Vector_Y$$

$$P_1P'_{2_{norm}} \times Vector_Y = Vector_Z$$

$$P_1P'_{2_{norm}} = Vector_X$$

$Vector_{X_x}$ is the x component of $Vector_X$, $Vector_{X_y}$ is the y component of $Vector_X$, and $Vector_{X_z}$ is the z component of $Vector_X$. Similarly, $Vector_{y_x}$ is the x component of $Vector_y$, $Vector_{y_y}$ is the y component of $Vector_y$, and $Vector_{y_z}$ is the z component of $Vector_y$. $Vector_{Z_x}$ is the x component of $Vector_Z$, $Vector_{Z_y}$ is the y component of $Vector_Z$, and $Vector_{Z_z}$ is the z component of $Vector_Z$. $P1_x$ is the x coordinate of P1, $P1_y$ is the y coordinate of P1, and $P1_z$ is the z coordinate of P1.

In some other embodiments, $$Tcamera = \begin{bmatrix} Vector_{X'_x} & Vector_{Y'_x} & Vector_{Z'_x} & P_{1'x} \\ Vector_{X'_y} & Vector_{Y'_y} & Vector_{Z'_y} & P_{1'y} \\ Vector_{X'_z} & Vector_{Y'_z} & Vector_{Z'_z} & P_{1'z} \\ 0 & 0 & 0 & 1 \end{bmatrix} \quad (2)$$

in which $$\overrightarrow{P_1P_{2_{norm}}} \times \overrightarrow{P_1P_{3_{norm}}} = Vector_Y$$

$$\overrightarrow{P_1P_{2_{norm}}} \times Vector_Y = Vector_Z$$

$$\overrightarrow{P_1P_{2_{norm}}} = Vector_X$$

$Vector_{X'_x}$ is the x component of $Vector_{X'}$, $Vector_{X'_y}$ is the y component of $Vector_{X'}$, and $Vector_{X'_z}$ is the z component of $Vector_{X'}$. Similarly, $Vector_{y'_x}$ is the x component of $Vector_{y'}$, $Vector_{y'_y}$ is the y component of $Vector_{y'}$, and $Vector_{y'_z}$ is the z component of $Vector_{y'}$. $Vector_{Z'_x}$ is the x component of $Vector_{Z'}$, $Vector_{Z'_y}$ is the y component of $Vector_{Z'}$, and $Vector_{Z'_z}$ is the z component of $Vector_{Z'}$. $P1'_x$ is the x coordinate of P1', $P1'_y$ is they coordinate of P1', and $P1'_z$ is the z coordinate of P1'.

Block 710 may be followed by block 720, "obtain conversion matrix." In some embodiments, the conversion matrix may be $T_{camera} T_{MRI}^{-1}$ and P1, P2, and P3 are transformed to the three-dimensional camera coordinate system according to $T_{camera} T_{MRI}^{-1}$. Assuming P1, P2, and P3 are transformed to $P1_{transformed}$, $P2_{transformed}$, and $P3_{transformed}$, respectively, a distance metric associated with differences between $P1_{transformed}$ and P1', $P2_{transformed}$ and P2', and $P3_{transformed}$ and P3' is calculated based on some feasible ICP approaches.

Block 720 may be followed by block 730. In block 730, whether the change of the distance metric reaches a threshold is determined. If the threshold is not reached, block 730 may go back to block 720 in which $P1_{transformed}$, $P2_{transformed}$, and $P3_{transformed}$ are selected to update $T_{camera}$ and eventually obtain new conversion matrix $T_{camera} T_{MRI}^{-1}$. If the threshold is reached, block 730 may be followed by block 740.

In block 740, a transform matrix is obtained to transform points from the three-dimensional camera coordinate system to the robotic arm coordinate system. In some embodiments, the transform matrix $$T_{robot} = \begin{bmatrix} & & & P_{C_x} \\ & R & & P_{C_y} \\ & & & P_{C_z} \\ 0 & 0 & 0 & 1 \end{bmatrix} \quad (5)$$

in which $$R = I + (\sin\theta)K + (1 - \cos\theta)K^2 \quad (4)$$

$$K = \begin{bmatrix} 0 & \frac{-k_z}{|\vec{k}|} & \frac{k_y}{|\vec{k}|} \\ \frac{k_z}{|\vec{k}|} & 0 & \frac{-k_x}{|\vec{k}|} \\ \frac{-k_y}{|\vec{k}|} & \frac{k_x}{|\vec{k}|} & 0 \end{bmatrix}$$

$$\theta = |\vec{k}|$$

$$I = \begin{bmatrix} 1 & 0 & 0 \\ 0 & 1 & 0 \\ 0 & 0 & 1 \end{bmatrix}$$

$\vec{k}$ is a rotation vector associated with a camera center (e.g., origin of the camera coordinate system) in the robotic arm coordinate system; kx is the x component of $\vec{k}$, ky is the y component of $\vec{k}$, and kz is the z component of $\vec{k}$; and Pcx is the x coordinate of the camera center, Pcy is the y coordinate of the camera center, and Pcz is the z coordinate of the camera center in the robotic arm coordinate system. In some embodiments, example approaches to register the camera center in the robotic arm coordinate system will be further described below in conjunction with FIG. 8.

According to the transform matrix, points on the operation pathway in the three-dimensional model coordinate system may be transformed to the robotic arm coordinate system. Therefore, the robotic arm may move to one or more points on the operation pathway.

Figure 8:
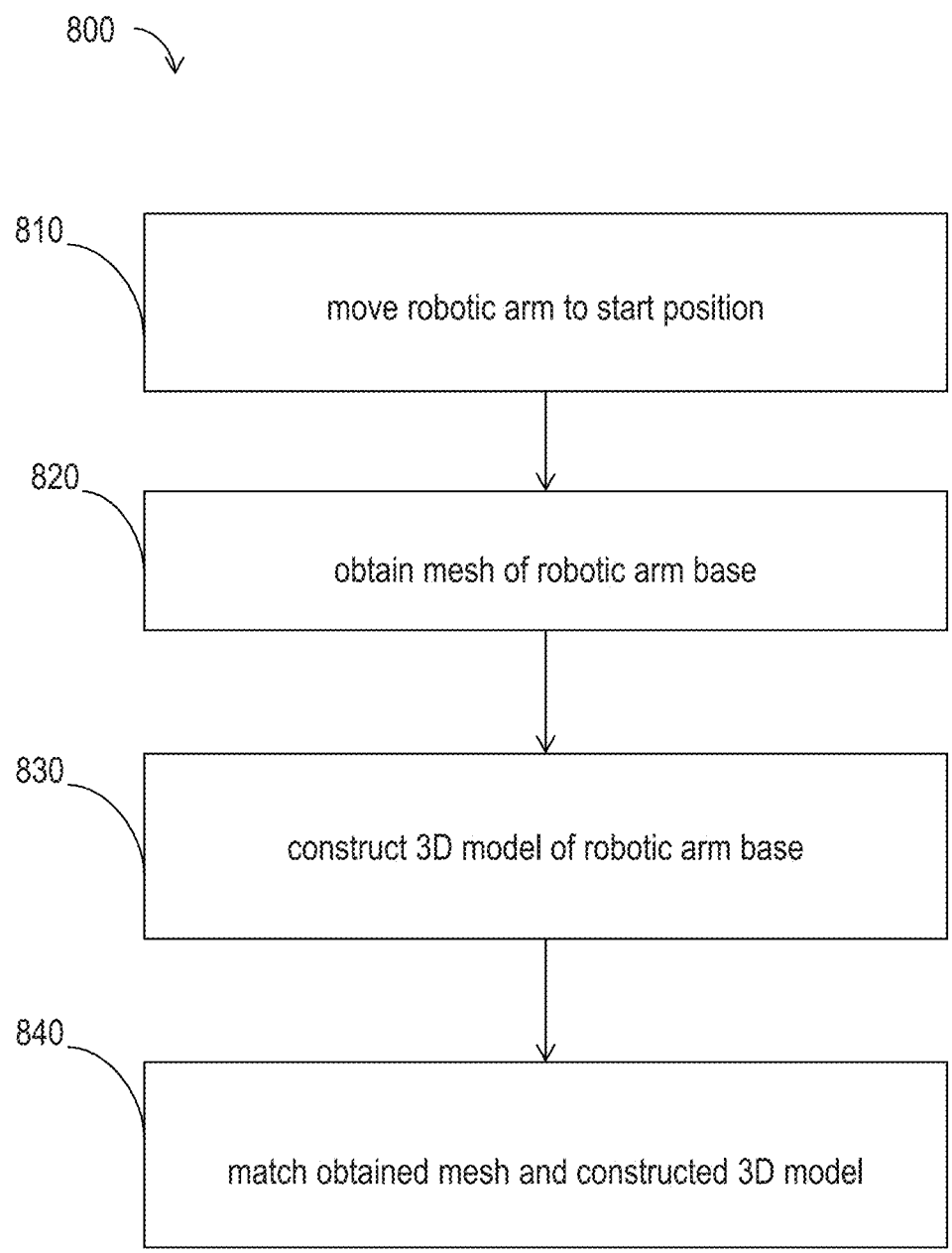
FIG. 8 is a flow diagram illustrating an example process to register an optical apparatus in the robotic arm coordinate system.

In some embodiments, FIG. 8 is a flow diagram illustrating an example process 800 to register an optical apparatus (e.g., camera) in the robotic arm coordinate system. In some embodiments, the optical apparatus may be mounted at a flange of the robotic arm. To describe the optical apparatus in the robotic arm coordinate system with kx, ky, kz, Pcx, Pcy, and Pcz as set forth above, a point associated with the optical apparatus (e.g., origin of the camera coordinate system) may be registered in the robotic arm coordinate system first according to process 800. Process 800 may include one or more operations, functions, or actions as illustrated by blocks 810, 820, 830 and/or 840, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

Process 800 may begin with block 810. In block 810, the robotic arm is configured to move to a start position. In some embodiments, the start position is adjacent to and facing a base of the robotic arm. In some embodiments, at the start position, the optical apparatus is configured to capture one or more images of the base of the robotic arm. The captured images are associated with spatial relationships between a point of the optical apparatus and the base of the robotic arm.

Block 810 may be followed by block 820. In block 820, a mesh of the base of the robotic arm is obtained based on the captured images.

Block 820 may be followed by block 830. In block 830, a three-dimensional model of the base of the robotic arm is constructed based on certain physical information of the robotic arm. In some embodiments, the physical information may include the dimension, orientation and/or geometric features of the elements of the robotic arm.

Block 830 may be followed by block 840. In block 840, the obtained mesh and the constructed three-dimensional model are matched. Some technical feasible approaches may be used for the matching, for example, iterative closest points approach may be used to match points of the obtained mesh and points of the constructed three-dimensional model to satisfy a given convergence precision. In response to the given convergence precision is satisfied, the spatial relationships between the point of the optical apparatus and the base of the robotic arm can be calculated. Based on the calculation, the point of the camera may be registered in the robotic arm coordinate system.

Figure 9:
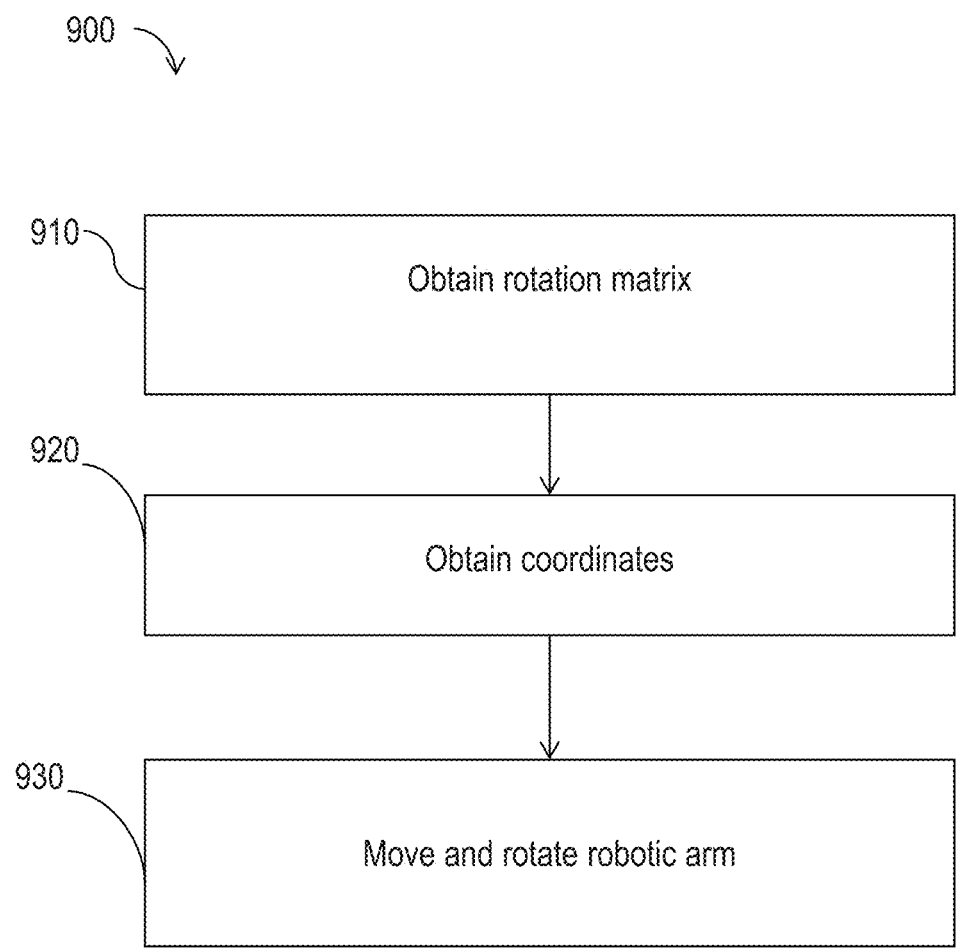
FIG. 9 is a flow diagram illustrating an example process to move robotic arm from an initial point to a safety point on an operation pathway.

FIG. 9 is a flow diagram illustrating an example process 900 to move robotic arm from an initial point to a safety point on an operation pathway, in accordance with some embodiments of the present disclosure. In some embodiments, the initial point is the point that an optical apparatus is configured to take images of the patient. In some embodiments, the initial point and the safety point are in the robotic arm coordinate system. Process 900 may include one or more operations, functions, or actions as illustrated by blocks 910, 920, and/or 930, which may be performed by hardware, software and/or firmware. The various blocks are not intended to be limiting to the described embodiments. The outlined steps and operations are only provided as examples, and some of the steps and operations may be optional, combined into fewer steps and operations, or expanded into additional steps and operations without detracting from the essence of the disclosed embodiments. Although the blocks are illustrated in a sequential order, these blocks may also be performed in parallel, and/or in a different order than those described herein.

In block 910, a rotation matrix for rotating the robotic arm from the initial point to the safety point is obtained. In some embodiments, the rotation matrix $R_s = R_x(\beta)R_z(\alpha)R_1$, in which $$R_z(\alpha) = \begin{bmatrix} \cos\alpha & -\sin\alpha & 0 \\ \sin\alpha & \cos\alpha & 0 \\ 0 & 0 & 1 \end{bmatrix}$$

-continued $$R_\chi(\beta) = \begin{bmatrix} \cos\beta & 0 & \sin\beta \\ 0 & 1 & 0 \\ -\sin\beta & 0 & \cos\alpha \end{bmatrix}$$

$R_1$ is the rotation matrix at the initial point;
α is the degrees of rotation along Z-axis at the initial point; and
β is the degrees of rotation along Y-axis at the initial point.

Block 910 may be followed by block 920. In block 920, coordinates of the safety point is obtained. In some embodiments, coordinates $(X_s, Y_s, Z_s)$ of the safety point may be:

$$\begin{bmatrix} & & & X_1 \\ R_1(3 \times 3) & & & Y_1 \\ & & & Z_1 \\ 0 & & & 1 \end{bmatrix} \begin{bmatrix} X_{dis} \\ Y_{dis} \\ Z_{dis} \end{bmatrix}$$

$R_1$ is the rotation matrix at the initial point;
$(X_1, Y_1, Z_1)$ are coordinates of the initial point;
$X_{dis}$ is a moving distance on X-axis from the initial point;
$Y_{dis}$ is a moving distance on Y-axis from the initial point; and
$Z_{dis}$ is a moving distance on Z-axis from the initial point.

In some embodiments, $X_{dis}$, $Y_{dis}$, and $Z_{dis}$ are associated with a length of the surgical instrument attached on the robotic arm. In some embodiments, the sum of the length of the surgical instrument and any of $X_{dis}$, $Y_{dis}$, and $Z_{dis}$ is smaller than the distance from the robotic arm to the patient on any X-axis, Y-axis, and Z-axis, respectively.

Block 920 may be followed by block 930. In block 930, robotic arm is configured to rotate and move according to the rotation matrix obtained in block 910 and the coordinates obtained in block 920 from the initial point to the safety point.

Figure 10:
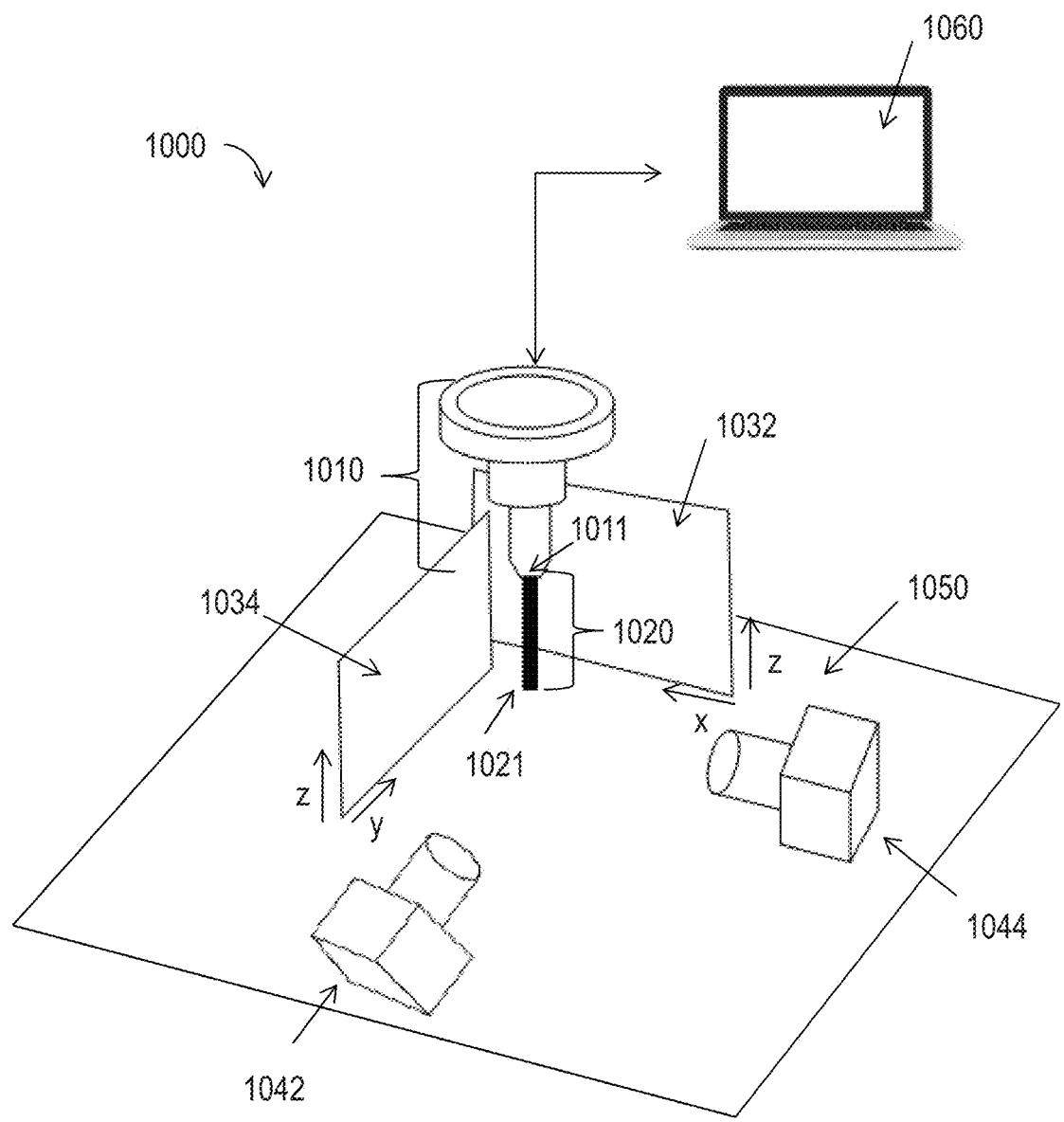
FIG. 10 is an example figure showing a system to register a surgical tool attached to a robotic arm flange in a robotic arm coordinate system.

In some embodiments, computing system 1060 of FIG. 10 may be configured to perform the aforementioned process 900.

FIG. 10 is an example figure showing a system 1000 to register a surgical tool attached to a robotic arm flange in the robotic arm coordinate system, in accordance with some embodiments of the present disclosure. In some embodiments, the robotic arm is at an initial point. In some embodiments, system 1000 may include flange 1010 of a robotic arm having edge 1011, surgical instrument 1020 attached to flange 1010 having tip 1021, first light source 1032, first camera 1042, second light source 1034, second camera 1044, and computing system 1060 coupled to the robotic arm either via a wired connection or a wireless connection. In some embodiments, light sources 1032 and 1034 may be back light plates perpendicularly disposed on plate 1050. In some embodiments, plate 1050 is defined by the robotic arm coordinate system through a technical feasible calibration approach using a standard probe attached on flange 1010. After calibration, the standard probe may be detached from flange 1010, and surgical instrument 1020 is then attached to flange 1010. Because plate 1050 is defined by the robotic arm coordinate system through the calibration, first back light plate 1032 may be defined by the x and z coordinates of the robotic arm coordinate system, and second back light plate 1034 may be defined by the y and z coordinates of the robotic arm coordinate system as shown in FIG. 10.

In some embodiments, light sources 1032 and 1034 are disposed perpendicularly with respect to each other. In some other embodiments, first camera 1042 is disposed on plate 1050 and is perpendicular to second light source 1034, and second camera 1044 is disposed on plate 1050 and is perpendicular to first light source 1032. Surgical instrument 1020 may be disposed among first light source 1032, second light source 1034, first camera 1042 and second camera 1044.

In some embodiments, first light source 1032 is configured to generate back light. The back light is configured to pass the body of surgical instrument 1020. First camera 1042 is configured to capture one or more images associated with surgical instrument 1020 (e.g., projections of surgical instrument on x-z plane of the robotic arm coordinate system) caused by the back light generated by first light source 1032.

Similarly, second light source 1034 is also configured to generate back light. The back light is configured to pass the body of surgical instrument 1020. Second camera 1044 is configured to capture one or more images associated with surgical instrument 1020 (e.g., projection of surgical instrument on y-z plane of the robotic arm coordinate system) caused by the back light generated by second light source 1034.

Figure 11:
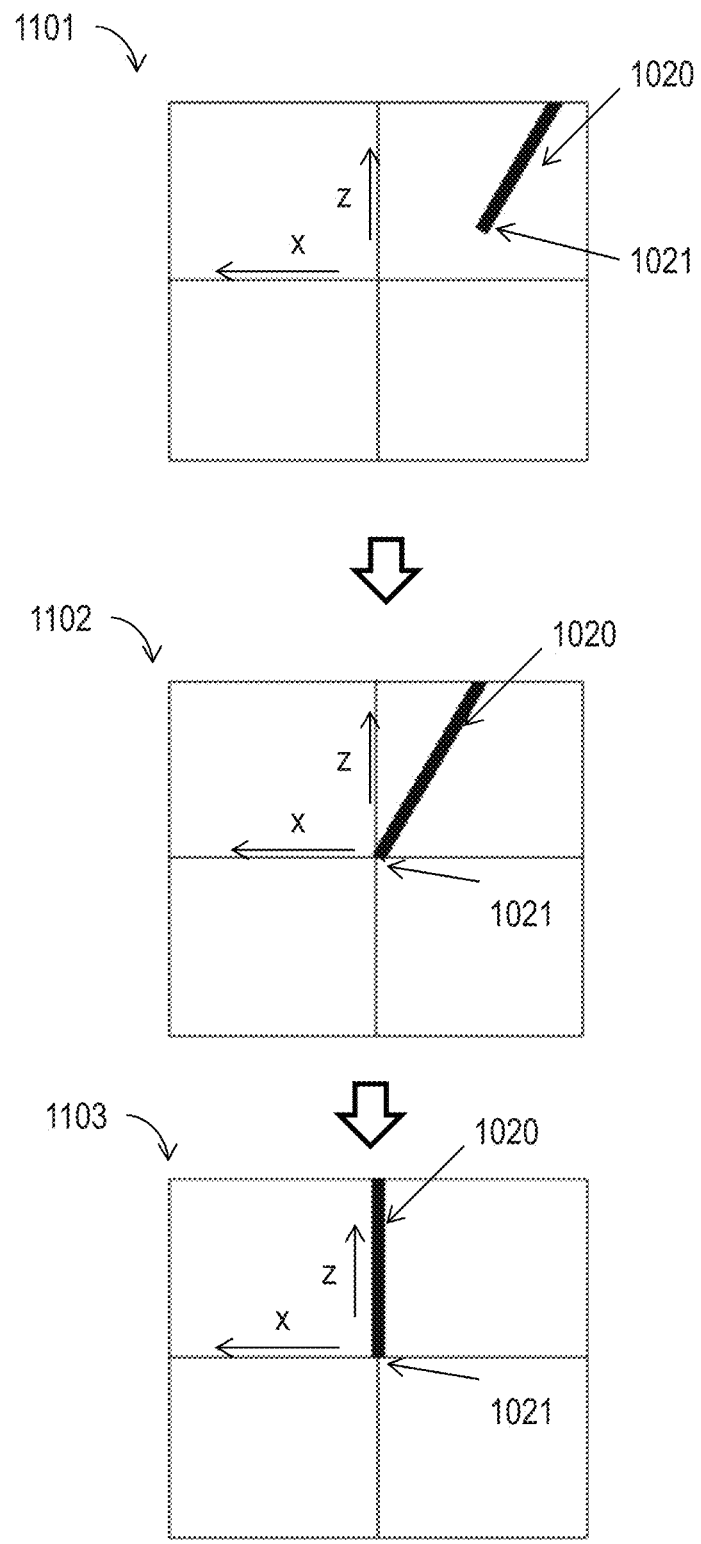
FIGS. 11 and 12 illustrate example images captured by a first camera and a second camera of the system to register a surgical tool attached to a robotic arm flange in a robotic arm coordinate system, all arranged in accordance with some embodiments of the present disclosure.

In conjunction with FIG. 10, FIG. 11 illustrates example images 1101, 1102, and 1103 captured by first camera 1042, in accordance with some embodiments of the present disclosure. As set forth above, in some embodiments, first camera 1042 is configured to capture one or more projections of surgical instrument 1020 on x-z plane of the robotic arm coordinate system. To register surgical instrument 1020 in the robotic arm coordinate system, in response to a first x-z plane projection of surgical instrument 1020 at a first state, having a first x-z plane projection of tip 1021 away from center of image 1101, computing system 1060 is configured to generate commands to move the robotic arm and flange 1010 and thus surgical instrument 1020 is moved to a second state. At the second state, a second x-z plane projection of surgical instrument 1020 is shown in image 1102 in which a second x-z plane projection of tip 1021 matches the center of image 1102. However, at the second state, the second x-z plane projection of surgical instrument 1020 is not aligned with z axis of the robotic arm coordinate system. In response, computing system 1060 is configured to generate commands to rotate the robotic arm and flange 1010 and thus surgical instrument 1020 is rotated to a third state. At the third state, a third x-z plane projection of surgical instrument 1020 is shown in image 1103 in which a third x-z plane projection of tip 1021 matches the center of image 1103 and the third x-z plane projection of surgical instrument 1020 is aligned with z axis of the robotic arm coordinate system.

Figure 12:
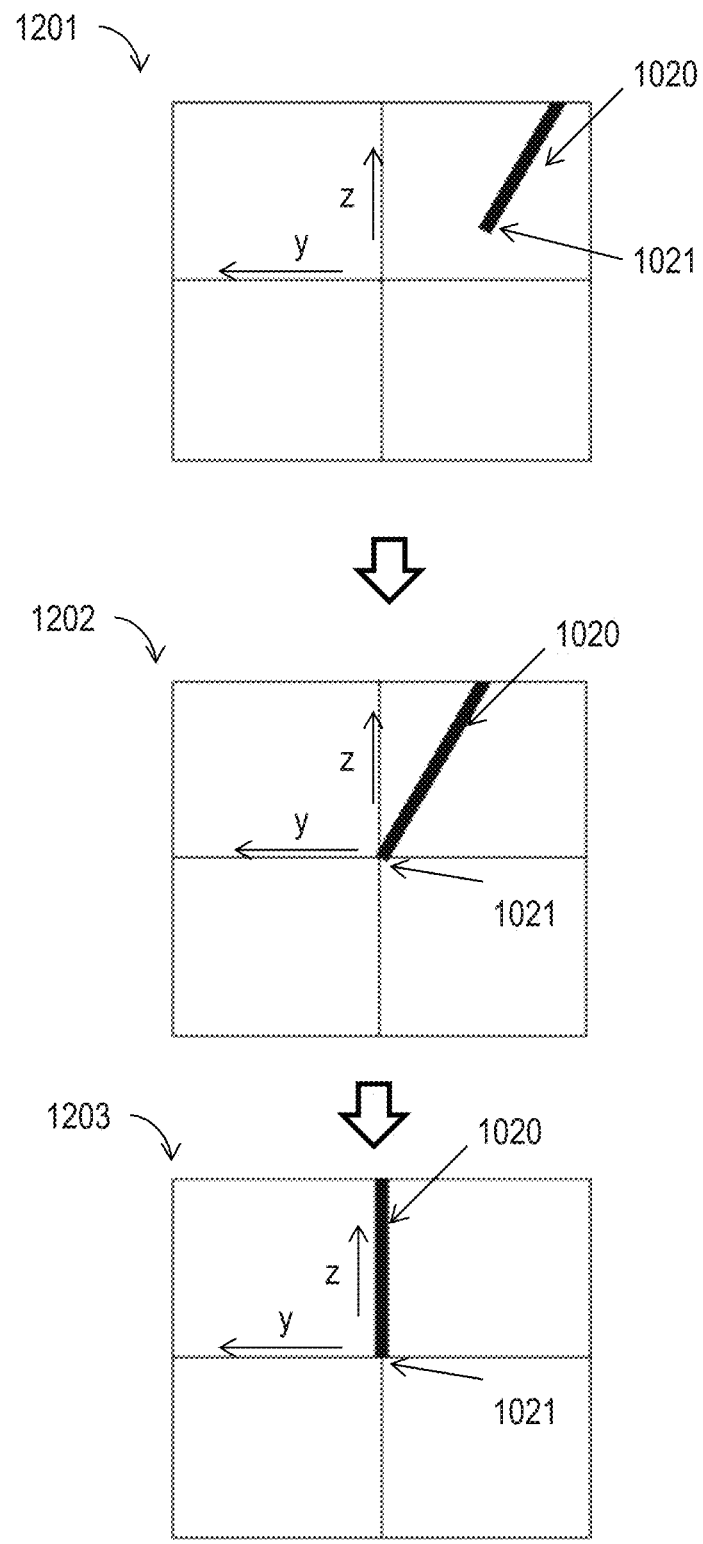

In addition to the steps described above, in conjunction with FIG. 10 and FIG. 11, FIG. 12 illustrates example images 1201, 1202, and 1203 captured by second camera 1044, in accordance with some embodiments of the present disclosure. As set forth above, in some embodiments, second camera 1044 is configured to capture one or more projections of surgical instrument 1020 on y-z plane of the robotic arm coordinate system. To register surgical instrument 1020 in the robotic arm coordinate system, in response to a first y-z plane projection of surgical instrument 1020 at a fourth state, having a first y-z plane projection of tip 1021 away from center of image 1201, computing system 1060 is configured to generate commands to move robotic arm and flange 1010 and thus surgical instrument 1020 is moved to a fifth state. At the fifth state, a second y-z plane projection of surgical instrument 1020 is shown in image 1202 in which a second y-z plane projection of tip 1021 matches the center of image 1202. However, at fifth state, the second y-z plane projection of surgical instrument 1020 is not aligned with z axis of the robotic arm coordinate system. In response, computing system 1060 is configured to generate commands to rotate the robotic arm and flange 1010 and thus surgical instrument 1020 is rotated to a sixth state. At the sixth state, a third y-z plane projection of surgical instrument 1020 is shown in image 1203 in which a third y-z plane projection of tip 1021 matches the center of image 1203 and the third y-z plane projection of surgical instrument 1020 is aligned with z axis.

In some embodiments, at the sixth state, first camera 1042 is configured to capture one or more projections of surgical instrument 1020 on x-z plane of the robotic arm coordinate system. In response to the sixth state also shows a x-z plane projection substantially the same as image 1103, computing system 1060 is configured to determine that a line corresponding to surgical instrument 1020, having a start point at edge 1011 of flange 1010 and an end point at tip 1021, is defined in the robotic arm coordinate system. Accordingly, coordinates of tip 1021 in the robotic arm coordinate system may be determined based on the coordinates of edge 1011 in the robotic arm coordinate system and geometry information (e.g., length) of surgical instrument 1021.

On the contrary, in response to the sixth state shows a x-z plane projection not substantially the same as image 1103, one or more steps described above for FIG. 11 and FIG. 12 are repeated until the sixth state shows a x-z plane projection substantially the same as image 1103.

In some embodiments, after determining the coordinates of tip 1021 in the robotic arm coordinate system, the robotic arm may be configured to contact tip 1021 to a reference point having known coordinates in the robotic arm coordinate system by moving and/or rotating the flange 1010 and surgical instrument 1020. In response to tip 1021 substantially touches the reference point, then computing system 1060 is configured to determine that coordinates of tip 1021 are verified. Otherwise, the steps set forth above may be repeated.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

We claim:

1. A method to drive a robotic arm to one or more points on an operation pathway, comprising:
    constructing a three-dimensional model based on a medical image scan of a patient;
    planning an operation pathway according to the three-dimensional model;
    retrieving image information of the patient captured by a three-dimensional optical apparatus;
    selecting a first set of landmark points in the three-dimensional model;
    selecting a second set of landmark points in the retrieved image information;
    matching the first set of landmark points with the second set of landmark points;
    transforming coordinates from a first coordinate system associated with the three-dimensional model to a second coordinate system associated with the three-dimensional optical apparatus based on a result of matching the first set of landmark points with the second set of landmark points; and
    driving the robotic arm to the one or more points on the operation pathway in a third coordinate system associated with the robotic arm, wherein the method further comprising:
    generating lights by a first light source and a second light source to form a plurality of projections of a surgical instrument attached to the robotic arm, wherein the first light source and the second light source are disposed perpendicular to each other, and wherein the projections are described in the third coordinate system;
        capturing, by a first camera, images with projections of the surgical instrument on x-z plane of the third coordinate system;
        capturing, by a second camera, images with projections of the surgical instrument on y-z plane of the third coordinate system;
        moving, by the robotic arm, the surgical instrument to align with z axis of the third coordinate system based on the images capture by the first camera and the images capture by the second camera;
    wherein the first camera and the second camera are disposed perpendicular to each other.

2. The method of claim 1, further comprising creating one or more binary images based on the medical image scan, wherein a white area of the binary images corresponds to an anatomical region on the operation pathway.

3. The method of claim 2, further comprising defining a first region and a second region of the binary images based on the white area.

4. The method of claim 3, wherein the selecting the first set of landmark points further comprises selecting one or more landmark points in the second region having a different gray scale value from the first region.

5. The method of claim 1, wherein the selecting the first set of landmark points comprises consistently selecting one or more landmark points in a first region of interest of the three-dimensional model.

6. The method of claim 5, wherein the selecting the second set of landmark points comprises consistently selecting one or more landmark points in a second region of interest of the retrieved image information.

7. The method of claim 6, wherein the first region of interest or the second region of interest includes a region defined by the nose tip, the eyes, the forehead, and a region between the eyebrows of the patient.

8. The method of claim 1, wherein the transforming coordinates further comprising registering a point of the three-dimensional optical apparatus in the third coordinate system.

9. The method of claim 8, further comprising transforming coordinates from the second coordinate system to the third coordinate system based on the registered point in the third coordinate system.

10. The method of claim 8, further comprising matching a mesh obtained by images of a part of the robotic arm captured by the three-dimensional optical apparatus with a three-dimensional model of the part of the robotic arm.

11. The method of claim 1, further comprising registering a surgical instrument attached to the robotic arm in the third coordinate system.

12. The method of claim 11, wherein the registering the surgical instrument is based on one or more projections of the surgical instrument in the third coordinate system.

13. The method of claim 1, wherein the planning the operation pathway further includes assigning a cost function to an anatomical region of the patient.

14. A system to drive a robotic arm to one or more points on an operation pathway, comprising:
a robotic arm;
a three-dimensional optical apparatus; and
a processor configured to:
construct a three-dimensional model based on a medical image scan of a patient;
plan an operation pathway according to the three-dimensional model;
retrieve image information of the patient captured by the three-dimensional optical apparatus;
select a first set of landmark points in the three-dimensional model;
select a second set of landmark points in the retrieved image information;
match the first set of landmark points with the second set of landmark points;
transform coordinates from a first coordinate system associated with the three-dimensional model to a second coordinate system associated with the three-dimensional optical apparatus based on a result of matching the first set of landmark points with the second set of landmark points; and
drive the robotic arm to the one or more points on the operation pathway in a third coordinate system associated with the robotic arm;
wherein the system further comprising a first light source and a second light source configured to generate light to form a plurality of projections of a surgical instrument attached to the robotic arm, wherein the projections are described in the third coordinate system;
wherein the first light source and the second light source are disposed perpendicular to each other;
wherein the system further comprising a first camera and a second camera disposed perpendicular to each other;
wherein the first camera is configured to capture images with projections of the surgical instrument on x-z plane of the third coordinate system;
wherein the second camera is configured to capture images with projections of the surgical instrument on y-z plane of the third coordinate system;
wherein the robotic arm moving the surgical instrument to align with z axis of the third coordinate system based on the images capture by the first camera and the images capture by the second camera.

15. The system of claim 14, wherein the processor is further configured to create one or more binary images based on the medical image scan, wherein a white area of the binary images corresponds to an anatomical region on the operation pathway.

16. The system of claim 15, wherein the processor is further configured to define a first region and a second region of the binary images based on the white area.

17. The system of claim 16, wherein the processor is further configured to select one or more landmark points in the second region having a different gray scale value from the first region.

18. The system of claim 14, wherein the processor is further configured consistently select one or more landmark points in a first region of interest of the three-dimensional model and/or one or more landmark points in a second region of interest of the retrieved image information.

19. The system of claim 14, wherein the processor is further configured to register a point of the three-dimensional optical apparatus in the third coordinate system and transform coordinates from the second coordinate system to the third coordinate system based on the registered point in the third coordinate system.

20. The system of claim 14, further comprising a first light source and a second light source configured to generate light to form a plurality of projections of a surgical instrument attached to the robotic arm, wherein the projections are described in the third coordinate system.

21. The system of claim 20, wherein the first light source and the second light source are disposed perpendicular to each other.

22. The system of claim 21, further comprising a first camera and a second camera disposed perpendicular to each other and configured to capture images of the projections.

23. The system of claim 14, wherein the system is configured to use in a brain operation, a nervous system operation, an endocrine operation, an eye operation, an ear operations, a respiratory operation, a circulatory system operation, a lymphatic operation, a gastrointestinal operation, a mouth and dental operation, an urinary operation, a reproductive operation, a bone, cartilage and joint operation, a muscle/soft tissue operation, a breast operations, and/or a skin operation.

* * * * *